United States Patent
Kozlowski et al.

[11] Patent Number: 5,935,958
[45] Date of Patent: Aug. 10, 1999

[54] MUSCARINIC ANTAGONISTS

[75] Inventors: Joseph A. Kozlowski, Princeton; Derek B. Lowe, Kenilworth; Wei K. Chang, Livingston; Sundeep Dugar, Bridgewater, all of N.J.

[73] Assignee: Schering Corporation, Kenilworth, N.J.

[21] Appl. No.: 08/883,183

[22] Filed: Jun. 26, 1997

Related U.S. Application Data

[60] Provisional application No. 60/021,171, Jul. 1, 1996.
[51] Int. Cl.$^6$ ............ A61K 31/495; A61K 31/445; C07D 401/12; C07D 405/14
[52] U.S. Cl. ............ 514/252; 514/235.8; 514/253; 514/254; 514/255; 544/121; 544/295; 544/360; 544/364; 544/365; 544/376; 544/377; 544/379; 544/398; 544/399; 544/400; 544/403
[58] Field of Search ............ 544/295, 360, 544/364, 365, 376, 377, 379, 121, 398, 399, 400, 403; 514/252–253, 255, 235.8, 254

[56] References Cited

U.S. PATENT DOCUMENTS

| | | | |
|---|---|---|---|
| 4,895,841 | 1/1990 | Sugimoto et al. | 514/212 |
| 5,110,901 | 5/1992 | Sugimoto et al. | 514/319 |
| 5,691,323 | 11/1997 | Thompson et al. | 544/295 |

FOREIGN PATENT DOCUMENTS

| | | |
|---|---|---|
| 0 028 449 | 5/1981 | European Pat. Off. . |
| 0 229 391 | 7/1987 | European Pat. Off. . |
| 0 321 175 | 6/1989 | European Pat. Off. . |
| 24 12 522 | 10/1974 | Germany . |
| 4-202185 | 7/1992 | Japan . |
| WO 92/10192 | 6/1992 | WIPO . |
| WO 93/08799 | 5/1993 | WIPO . |
| WO 94/12493 | 6/1994 | WIPO . |
| WO 96/26196 | 8/1996 | WIPO . |

OTHER PUBLICATIONS

Quirion et al, *TIPS* pp. 80–84 (Dec. 1989).
Gray et al, *TIPS* pp. 85–88 (Dec. 1989).
Melchiorre et al, *J. Med. Chem.* 36 p. 3734 (1993).
Baumgold et al., *Eur. J. Pharmacol.*, 251, (1994) 315–317.
Logermann et al, *Brit. J. Pharmacol.*, 17 (1961), pp. 286–296.
Cheng et al, *Biochem. Pharmacol.*, 22 (1973), pp. 3099–3108.
Watson et al, *J. Pharmacol. Exp. Ther.*, 237 (1986), pp. 411–418.
Sindelar, et al, *Collect. Czech Chem. Commun.*, 54 (8) (1989), pp. 2240–2247.
Evans et al, *J. Med. Chem.*, 27, 9 (1984), pp. 1127–1131.

*Primary Examiner*—Emily Bernhardt
*Attorney, Agent, or Firm*—A. W. Magatti

[57] ABSTRACT

Di-N-substituted piperazine or 1,4-di-substituted piperidine compounds in accordance with formula I (including all isomers, salts, esters, and solvates)

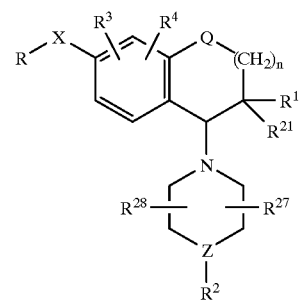

wherein Q, n, R, $R^1$, $R^2$, $R^3$, $R^4$, $R^{21}$, $R^{27}$, $R^{28}$, X, and Z are as defined herein are muscarinic antagonists useful for treating cognitive disorders such as Alzheimer's disease. Pharmaceutical compositions and methods of preparation are also disclosed. Also disclosed are synergistic combinations with acetyl-cholinesterase inhibitors of compounds capable of enhancing acetylcholine release and having the above formula.

16 Claims, No Drawings

MUSCARINIC ANTAGONISTS

This application claims the benefit of U.S. Provisional Application No. 60/021,171 filed Jul. 1, 1996.

FIELD OF THE INVENTION

The present invention relates to di-N-substituted piperazines and 1,4-di-substituted piperidines useful in the treatment of cognitive disorders, pharmaceutical compositions containing the compounds, methods of treatment using the compounds, and to the use of said compounds in combination with acetylcholinesterase inhibitors.

BACKGROUND OF THE INVENTION

Alzheimer's disease and other cognitive disorders have received much attention lately, yet treatments for these diseases have not been very successful. According to Melchiorre et al. (*J. Med. Chem.* (1993), 36, 3734–3737), compounds that selectively antagonize m2 muscarinic receptors, especially in relation to m1 muscarinic receptors, should possess activity against cognitive disorders. Baumgold et al. (*Eur. J. Pharmacol.*, 251, (1994) 315–317) disclose 3-α-chloroimperialine as a highly selective m2 muscarinic antagonist.

The present invention is predicated on the discovery of a class of di-N-substituted piperazines and 1,4-di-substituted piperidines. Logemann et al. (*Brit. J. Pharmacol.* (1961), 17, 286–296) describe certain di-N-substituted piperazines, but these are different from the inventive compounds of the present invention. Furthermore, the compounds of Logemann et al. are not disclosed to have activity against cognitive disorders.

International Patent Publication Number WO93/08799 published May 13 1993 (Smith-Kline Beecham) discloses inter alia indane derivatives that are endothelin receptor antagonists and are (in part) of the following formula:

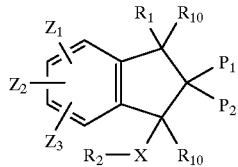

wherein:
$R_1$ is —X(CH$_2$)$_n$Ar or —X(CH$_2$)$_n$R$_8$;
$R_2$ is H or Ar;
$P_1$ is —X(CH$_2$)$_n$R$_8$;
$P_2$ is —X(CH$_2$)$_n$R$_8$ or —XR$_9$Y;
$R_8$ is H, alkyl, alkenyl, alkynyl, CO$_2$H, CO$_2$alkyl, or CO$_2$Ar;
$R_9$ is alkyl, alkenyl or phenyl;
$R_{10}$ is H, alkyl (which may be substituted with CO$_2$H, CO$_2$alkyl or CO$_2$(CH$_2$)$_n$Ar), alkenyl, phenyl, OH, alkoxy, S(O)$_q$alkyl, S(O)$_q$alkenyl, S(O)$_q$aryl, NH$_2$, NHalkyl, N(alkyl)$_2$, F, Cl, Br, I, CF$_3$, NHCHO, NHCOalkyl, —X(CH$_2$)$_n$R$_8$ or —XR$_9$Y;
X is (CH$_2$)$_n$, O, NH, Nalkyl, or S(O)$_q$;
Y is CH$_3$ or X(CH$_2$)$_n$Ar;
Ar is a variety of substituted or unsubstituted heterocyclic and aromatic hydrocarbon groups, including piperidinyl and piperazinyl, which may carry substituents;

$Z_1$ and $Z_2$ are independently H, alkyl, alkenyl, alkynyl, OH, alkoxy, S(O)$_q$alkyl, NH$_2$, NHalkyl, N(alkyl)$_2$, F, Cl, Br, I, CF$_3$, NHCHO, NHCOalkyl, —X(CH$_2$)$_n$R$_8$, phenyl, benzyl or cycloalkyl;
$Z_3$ is $Z_1$ or —XR$_9$Y;
n is 0 or an integer from 1 to 6, and q is 0, 1 or 2;
and the groups designated as 'alkyl', 'alkenyl', 'alkynyl' or 'phenyl' can all be substituted.

(The definitions of radicals as given in that patent do not in general pertain to the present invention, even though similar symbols may be used.)

SUMMARY OF THE INVENTION

The present invention relates to compounds according to the structural formula I,

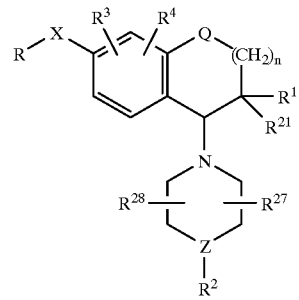

including all stereoisomers and pharmaceutically acceptable salts, esters, and solvates thereof, wherein:
Z is N, CH or C—alkyl;
X is —O—, —S—, —SO—, —SO$_2$—, —CO—, —CH$_2$—, —CONR$^{20}$—, —NR$^{20}$—SO$_2$—, —NR$^{20}$CO—, or —SO$_2$—NR$^{20}$—;
Q is —O—, —S—, —SO—, —SO$_2$—, or —CH$_2$—;
R is

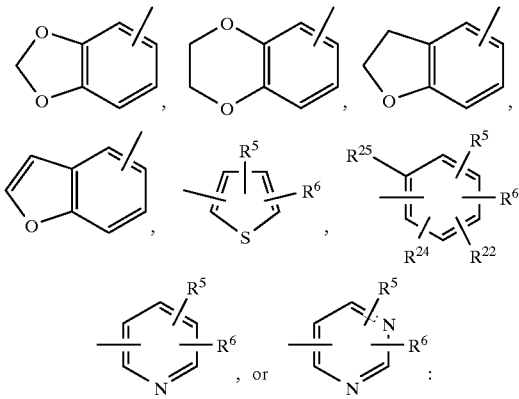

$R^1$ and $R^{21}$ are independently selected from the group consisting of hydrogen, alkyl, alkenyl, cycloalkyl, cycloalkenyl, cycloalkylalkyl, cycloalkenylalkyl, phenylalkyl, and hydroxyalkyl;
$R^2$ is cycloalkyl, cycloalkyl substituted with 1 to 3 independently selected $R^3$ groups, cycloalkenyl, cycloalkylalkyl,

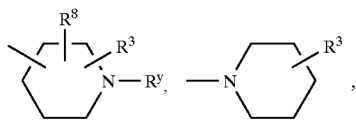

(wherein $R^y$ is H, alkyl, alkenyl, $SO_2R^z$ or $COR^z$ wherein $R^z$ is alkyl, alkenyl, aryl, heteroaryl, or cycloalkyl), with the proviso that $R^2$ is $R^3$-substituted-1-piperidinyl only when Z is CH or C-alkyl; or, when Z is CH, $R^2$ may also be alkoxycarbonyl, —N($R^9$)(hydroxyalkyl) wherein $R^9$ is H, hydroxyalkyl, or alkyl, or —N($R^9$)$_2$ wherein the two $R^9$ groups may be joined to form an alkylene group;

$R^3$, $R^4$, $R^5$, $R^6$, $R^{22}$, $R^{24}$, and $R^{25}$ are independently selected from the group consisting of H, alkyl, halo, alkoxy, benzyloxy, benzyloxy substituted by nitro or aminoalkyl, polyhaloalkyl, nitro, sulfonyl, hydroxy, amino, alkylamino, formyl, alkylthio, acyloxy, alkylsulfonyl, arylsulfonyl, acyl, alkoxycarbonyl, alkylsulfinyl, —OCONH$_2$, —OCONH—alkyl, —OCON(alkyl)$_2$, —NHCOO—alkyl, —NHCO—alkyl, phenyl, hydroxyalkyl, and 1-morpholinyl;

$R^8$ is hydrogen, lower alkyl or cyclopropyl;

$R^{20}$ is H, phenyl or alkyl;

$R^{27}$ and $R^{28}$ are independently selected from the group consisting of H, alkyl, hydroxyalkyl, alkoxyalkyl, arylalkyl, mercaptoalkyl, alkylthioalkyl, and carboxyalkyl, and additionally $R^{27}$ and $R^{28}$ may be joined to form an alkylene group; and n is 0 or an integer from 1 to 3.

Another aspect of the invention is a pharmaceutical composition which comprises a compound having structural formula I as defined above, including stereoisomers, pharmaceutically acceptable salts, esters, and solvates thereof, in combination with a pharmaceutically acceptable carrier.

Another aspect of the invention is the use of a compound of formula I as defined above, including stereoisomers, pharmaceutically acceptable salts, esters, and solvates thereof, for the preparation of a pharmaceutical composition useful in the treatment of cognitive disorders and neurodegenerative diseases such as Alzheimer's disease.

Yet another aspect of the invention comprises a method for making a pharmaceutical composition comprising mixing a compound of formula I as defined above, including stereoisomers, pharmaceutically acceptable salts, esters, and solvates thereof, with a pharmaceutically acceptable carrier.

Another aspect of this invention is a method for treating a cognitive or neurodegenerative disease comprising administering to a patient suffering from said disease an effective amount of a compound of formula I as defined above, including stereoisomers, pharmaceutically acceptable salts, esters, and solvates thereof.

Another aspect of this invention is a method for treating cognitive and neurodegenerative diseases, such as Alzheimer's disease, with a compound of formula I as defined above, including stereoisomers, pharmaceutically acceptable salts, esters, and solvates thereof, in combination with an acetylcholinesterase inhibitor.

Another aspect of this invention is a method for treating a cognitive or neurodegenerative disease comprising administering to a patient suffering from said disease an effective amount of a combination of a compound of formula I as defined above, including stereoisomers, pharmaceutically acceptable salts, esters, and solvates thereof, said compound being capable of enhancing acetylcholine release (and being preferably an m2 or m4 selective muscarinic antagonist), together with an acetylcholinesterase inhibitor.

Another aspect of this invention is a kit comprising in separate containers in a single package pharmaceutical compounds for use in combination to treat cognitive disorders, wherein one container contains a compound of formula I as defined above, including stereoisomers, pharmaceutically acceptable salts, esters, and solvates thereof, said compound being capable of enhancing acetylcholine release (and preferably being an m2 or m4 selective muscarinic antagonist) in a pharmaceutically acceptable carrier, and a second container contains an acetylcholinesterase inhibitor in a pharmaceutically acceptable carrier, the combined quantities being an effective amount.

DETAILED DESCRIPTION OF THE PREFERRED EMBODIMENTS

In a particularly preferred group of compounds of the formula I, Z is N. In another preferred group, n is 1 or 2 or especially 0.

In another preferred group of compounds, X is SO or especially O or $SO_2$.

In yet another preferred group of compounds, $R^8$ is H or methyl.

In another preferred group of compounds, R is

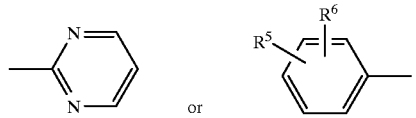

(wherein $R^5$ and $R^6$ are H, $CH_3$, nitro, $NH_2$, acetylamino, or methoxy), especially 4-methoxyphenyl; X is preferably O, SO or $SO_2$, $R^3$ and $R^4$ are H, and $R^1$ is H, cycloalkyl, cycloalkylalkyl or alkyl, and $R^{21}$ is H.

In another preferred group of compounds, $R^3$ and $R^4$ are H, and $R^1$ is H, cycloalkyl or alkyl and $R^{21}$ is H. $R^1$ is preferably H, $CH_3$ or cyclohexylmethyl, and $R^2$ is cyclohexyl.

In another preferred group of compounds, $R^3$ and $R^4$ are H, X is O, SO or $SO_2$, and $R^1$ is H, cycloalkyl or alkyl and $R^{21}$ is H. $R^1$ is preferably H or $CH_3$.

In another preferred group of compounds, at least one of $R^{27}$ and $R^{28}$ is alkyl. In particular, at least one of $R^{27}$ and $R^{28}$ is alkyl and the other is H or alkyl; more preferably, one of $R^{27}$ and $R^{28}$ is methyl and the other is hydrogen.

In another preferred group of compounds, R is 4-methoxyphenyl.

In a particularly preferred group of compounds of the formula I:

R is a phenyl group, which may be substituted with nitro or especially with methoxy, where each of these groups is preferably in the 4-position, or in particular a 2-pyrimidinyl group;

X is S, SO, or especially $SO_2$ or O;

Q is O or especially $CH_2$;

n is 1 or 2 or especially 0;

$R^1$ is H and $R^{21}$ is cyclohexylmethyl;

$R^{27}$ and $R^{28}$ are $CH_3$ or especially H;

Z is N; and $R^2$ is cyclohexyl or 1-piperidinyl.

Except where stated otherwise the following definitions apply throughout the present specification and claims. These definitions apply whether a term is used by itself or in combination with other terms. For example, the definition of "alkyl" applies not only to "alkyl" but also to the "alkyl" portions of "alkoxy", "polyhaloalkyl", etc.

Alkyl represents a straight or branched saturated hydrocarbon chain having 1 to 20 carbon atoms, preferably 1 to 8 carbon atoms. A "lower alkyl" group has 1 to 6 carbon atoms, preferably 1 to 4 carbon atoms.

Alkenyl represents a straight or branched hydrocarbon chain of from 3 to 15 carbon atoms, more preferably 3 to 12 carbon atoms, having at least one carbon-to-carbon double bond but the free valency at least one carbon atom removed from the double bond.

Cycloalkyl represents a saturated carbocyclic ring having 3 to 12 carbon atoms.

Cycloalkenyl represents a carbocyclic ring having from 5 to 8 carbon atoms and at least one carbon-to-carbon double bond in the ring.

Acyl represents a radical of a carboxylic acid and thus includes groups of the formula Alkyl—CO—, Aryl—CO—, Aralkyl—CO—, Cycloalkyl—CO—, wherein the various hydrocarbon radicals are as defined in this section.

Halo represents fluoro, chloro, bromo or iodo.

Aryl represents phenyl or naphthyl, each of which may be substituted with one to three groups $R^c$ selected from halo, alkyl, hydroxy, alkoxy, phenoxy, amino, alkylamino and dialkylamino groups. Preferred aryl groups are phenyl, substituted phenyl, 1-naphthyl, 2-naphthyl and indanyl groups.

Heteroaryl represents a cyclic group having at least one O, S and/or N interrupting a carbocyclic ring structure and having a sufficient number of pi electrons to provide aromatic character. The aromatic heterocyclic group preferably has from 2 to 14, especially from 3 to 9 carbon atoms, e.g., 2-, 3- or 4-pyridyl, 2- or 3-furyl, 2- or 3-thienyl, 2-, 4- or 5-thiazolyl, 2-, 4- or 5 4-, 5- or especially 2-pyrimidinyl, 2-pyrazinyl, 3- or 4-pyridazinyl, 3-, 5- or 6-[1,2,4-triazinyl], 3- or 5-[1,2,4-thiadiazolyl], 2-, 3-, 4-, 5-, 6- or 7-benzofuranyl, 2-, 3-, 4-, 5-, 6- or 7-indolyl, 3-, 4- or 5-pyrazolyl, or 2-, 4- or 5-oxazolyl, etc.

Preferred heteroaryl groups include 2-, 3- or 4-pyridyl, 2- or 3-furyl, 2- or 3-thienyl, 2-, 4- or 5-imidazolyl, and 7-indolyl.

Polyhalo indicates substitution of at least 2 halo atoms in the group modified by the term "polyhalo".

Sulfonyl represents a group of the formula $-SO_2-$.

Sulfinyl represents a group of the formula $-SO-$.

Alkylene represents a straight or branched saturated hydrocarbon chain having 1 to 20 carbon atoms, preferably 1 to 8 carbon atoms, and two free valencies, which for the purpose of this invention are not on the same carbon atom when the alkylene group has 2 to 20 carbon atoms. Preferred alkylene groups are methylene or polymethylene groups of the formula $-(CH_2)_{(2\text{-}20)}-$.

Each radical or group that appears more than once in a structural formula, for example $R^9$ when $R^2$ is $-N(R^9)_2$, may be independently selected from the whole definition for that radical or group.

Compounds of this invention may exist in at least two stereoisomeric configurations based on the asymmetrically substituted carbon atom to which the group

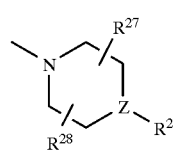

is attached. Further stereoisomerism may be present, for example when $R^1$ and $R^{21}$ are not identical, or when X is SO, or when at least one of $R^{27}$ and $R^{28}$ is not hydrogen. All possible stereoisomers of formula I are within the scope of the invention.

Compounds of formula I can exist in unsolvated as well as solvated forms, including hydrated forms. In general, the forms that are solvated with pharmaceutically acceptable solvents such as water, ethanol and the like, are equivalent to the unsolvated forms for the purposes of this invention.

A compound of formula I may form pharmaceutically acceptable salts with organic and inorganic acids. Examples of suitable acids for salt formation are hydrochloric, sulfuric, phosphoric, acetic, citric, malonic, salicylic, malic, fumaric, succinic, ascorbic, maleic, methanesulfonic and other mineral and carboxylic acids well known to those skilled in the art. A salt is prepared by contacting a free base form with a sufficient amount of the desired acid to produce a salt in the conventional manner. The free base form may be regenerated by treating the salt with a suitable dilute aqueous base such as dilute aqueous sodium hydroxide, potassium carbonate, ammonia or sodium bicarbonate. The free bases differ from the corresponding salts somewhat in certain physical properties, such as solubility in polar solvents, but the salts are otherwise equivalent to the corresponding free bases for purposes of the invention.

Compounds of formula I and their salts can be prepared by standard methods. The methods of the following Schemes are preferred; the starting materials either are known or can be prepared by standard methods, and the radicals in the formulae (unless otherwise stated) have the meanings given for formula I, with the proviso that $R^2$ can also be a nitrogen-protecting group that is replaced (e.g., at the end of the Scheme) with a group $R^2$ according to formula I:

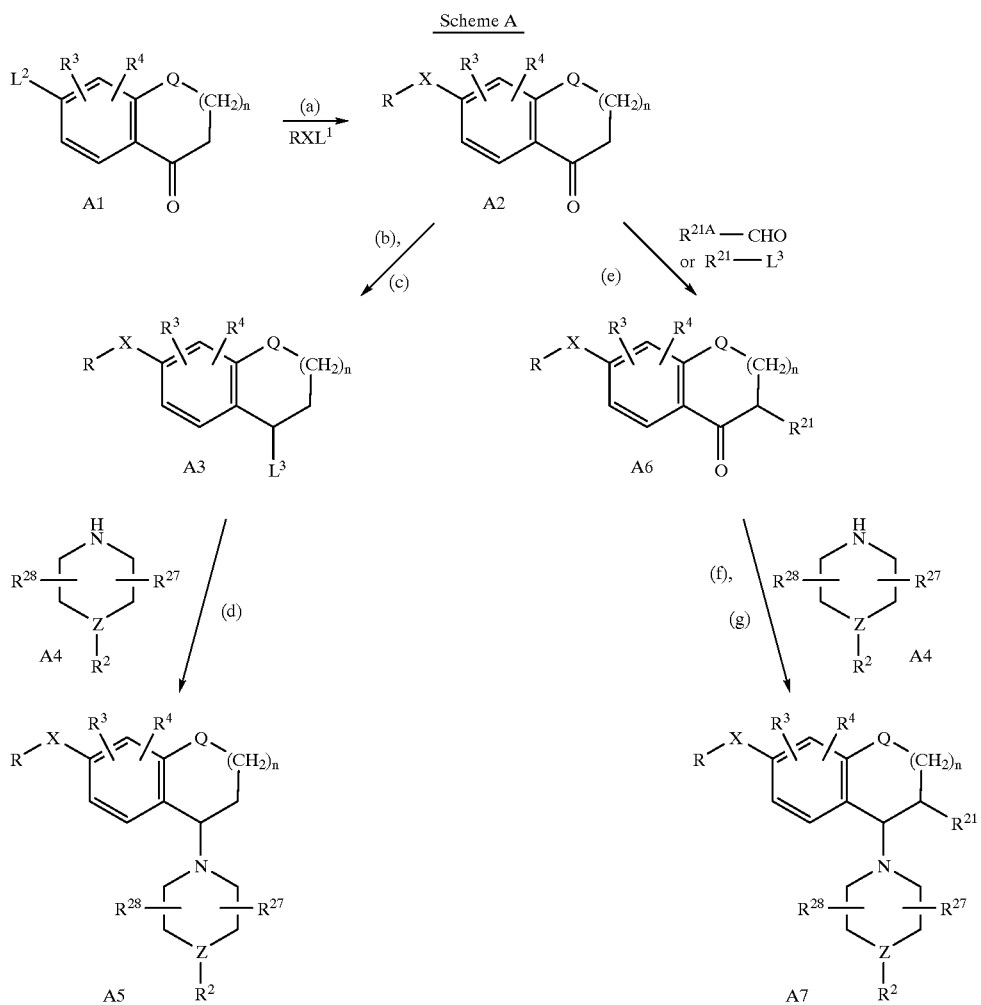

Scheme A

In Scheme A, Q can be —O—, —S—, or —CH$_2$—. In Step (a), L$^1$ and L$^2$ are groups that can be eliminated during the reaction. L$^2$ is preferably a leaving group such as a halogen atom, especially bromine or fluorine, and L$^1$ is preferably an alkali metal, e.g., sodium or potassium. The reaction is carried out in an inert organic solvent, which is preferably anhydrous, e.g., DMSO, DMF, or a polar ether such as dimethoxyethane.

When X is O or S, the reactant contributing the group X can be prepared by reaction of the parent compound containing the group XH and an alkali metal hydride in situ in the inert organic solvent.

Step (b) comprises the reduction of the carbonyl group to hydroxy methylene with a reducing agent such as an aluminum hydride, e.g., lithium aluminum hydride, or a borohydride, e.g., sodium borohydride, in an inert organic solvent. When an aluminum hydride is used, the solvent should be anhydrous and is preferably an ether solvent such as THF; when a borohydride is used, the solvent can be a lower alkanol, especially methanol or ethanol, or THF, DMF, or DMSO, all of which may be anhydrous or aqueous. Step (c) comprises the conversion of the hydroxy group into a leaving group L$^3$, e.g., a sulfonate ester group such as a group SO$_3$—(lower alkyl) or with a halogen atom, especially bromine or iodine. This conversion can be carried out with a sulfonyl chloride, e.g., methane-, ethane- or 4-toluene-sulfonylchloride, and an organic base, e.g., a tertiary amine such a pyridine or triethylamine; or with a halogenating agent, e.g., SOCl$_2$ or PBr$_3$, if desired with displacement of the resulting bromide by iodide when an iodide is required.

Step (d) comprises the amination of the reactive group L$^3$, e.g. Cl, with a piperidine or piperazine to form the desired product of the formula I. This reaction can be carried out neat with the piperidine or piperazine or in an organic solvent, and an acid-binding agent can if desired be used. An excess of the piperidine or piperazine may serve both as acid-binding agent and as organic solvent. When a piperazine is used, its second nitrogen atom can bind the acid liberated in the reaction and no extra acid-binding agent may be necessary.

Step (e) can be carried out by condensation of the reactants in the presence of a basic catalyst, e.g, an amine such as piperidine. Under these circumstances an excess of the catalyst can serve as solvent. Alternatively, the reaction can be effected in the presence of a strongly basic catalyst such as LDA (lithium diisopropylamide) or lithium HMDS (lithium hexamethyldisilazane), which preferably is added at a low temperature, e.g., −78° C. to 0° C., in an inert anhydrous organic solvent such as THF or diethyl ether. The reaction with the aldehyde may then be effected at a low temperature, at room temperature or at moderately elevated temperature, e.g., at −78 to +60° C., preferably about 0 to +30° C., and under an inert atmosphere, e.g., nitrogen. When the aldehyde $R^{21A}$ —CHO is used to introduce the group $R^{21}$, then $R^{21A}$ has one carbon atom fewer than $R^{21}$ such that $R^{21A}$—$CH_2$ is $R^{21}$. The intermediate carbinol of the formula

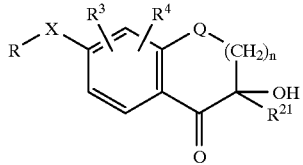

can then be dehydrated (for example, direct with acid or, after conversion of the hydroxy group into a leaving group, e.g., a halide or sulfonate, with base), and the resulting compound with a double bond can be hydrogenated, e.g. with hydrogen and a catalyst such as Pd/C, to the compound of the formula A6. When the hydrogenation also reduces the carbonyl group, then the reduction of the following Step (f) can be obviated.

Step (f) can then be carried out by the methods of Steps (b) (reduction) and (c) (conversion of the hydroxy group into a leaving group $L^3$) above, and Step (g) by the method of Step (d) above.

If it is desired to introduce a group $R^1$ in addition to $R^{21}$, then the process of Step (e) can be repeated before Steps (f) and (g) are carried out.

An alternative method for preparing compounds of the formulae A5 and A7 in Scheme A comprises the condensation of a compound of the formula A2 or A6 with a compound of the formula A4, followed by the reduction of the resulting condensation product, e.g., imine, preferably in the same step. The condensation can be effected in the presence of a compound or compounds serving as a mild Lewis acid (or a protic acid) and a dehydrating agent. The mild Lewis acid is conveniently a titanium tetra(lower alkoxide), especially $Ti(O-2-Pr)_4$, which is commercially available and gives good results. The resulting condensation product (e.g., imine) can then be reduced with a mild reducing agent, e.g., a sodium borohydride, but preferably one that is not reactive towards the Lewis acid or protic acid, especially sodium cyanoborohydride. Alternatively, the reaction can be effected with sodium triacetoxyborohydride as both Lewis acid and reducing agent, in the presence of acetic acid.

The condensation and reduction is carried out in the presence of an inert organic solvent, preferably a chlorinated hydrocarbon, e.g., 1,2-dichloroethane or especially methylene chloride.

Scheme B

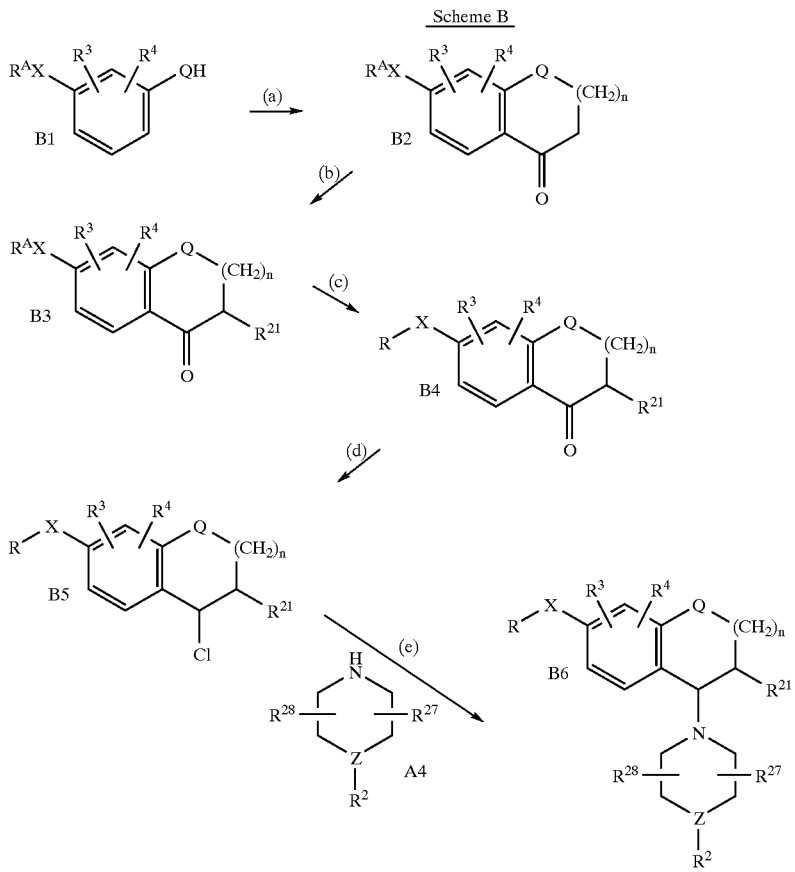

In Scheme B, Q is —O— or —S—. In Step (a) the compound of the formula B1 (wherein $R^A$ is R or preferably H) is reacted with a reactive derivative of an acid of the formula $L^4.(CH_2)_n.CH_2.CO_2H$, or such an acid with a substituent $R^1$ and/or $R^{21}$ on the 2-carbon atom, wherein $L^4$ is a reactive group such as a chlorine or bromine atom. The reactive derivative is preferably the acid chloride, but may be the bromide or anhydride. The reaction is effected under Friedel-Crafts conditions with a catalyst and inert organic solvent; the catalyst is for example anhydrous aluminum chloride or boron trifluoride, and the solvent is preferably nitrobenzene. The reaction is typically started at low temperature, e.g., at 0–20° C., and continued at moderately elevated temperature, e.g., 30–100° C.

A group $R^{21}$ (where $R^{21}$ is other than hydrogen) may be introduced in Step (b) as described under Scheme A above. When the group $R^A$ is hydrogen, the group R may be introduced in Step (c) by reaction of the starting material with a compound of the formula $RL^4$, wherein $L^4$ is a leaving group, e.g., a sulfonate ester group but preferably a halogen, especially Cl or Br. The reaction is preferably carried out in an organic solvent in the presence of a strong inorganic base, e.g., sodium or potassium hydride or hydroxide, and an inert organic solvent, e.g. anhydrous DMSO, DMF, or a polar ether such as dimethoxyethane. Steps (d) and (e) may then be carried out as described under Scheme A above for Steps (b), (c) and (d) therein.

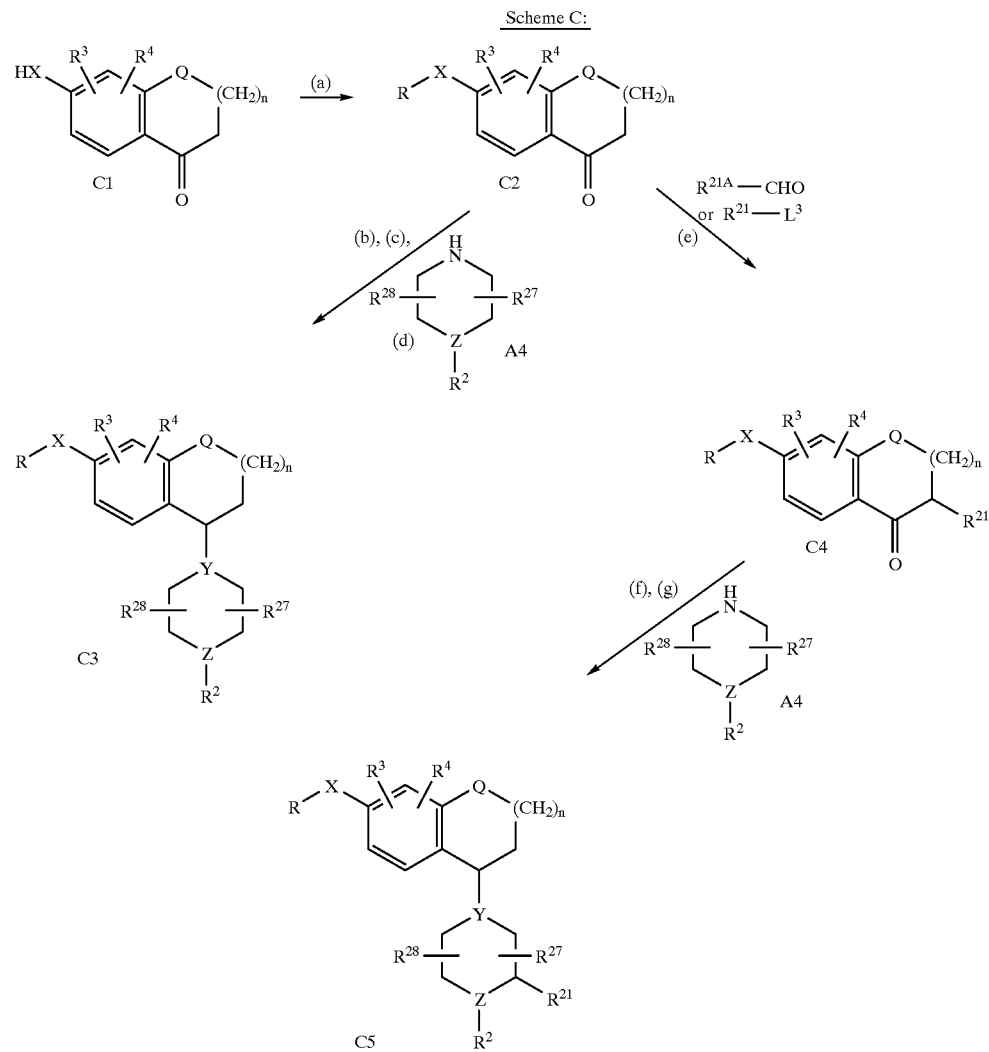

In Scheme C, Q is O or S. In Step (a), the group R is introduced by reaction of the starting material with a compound of the formula $RL^4$, wherein $L^4$ is a leaving group, as described under Step (c) of Scheme B above. The remaining steps (b) through (g) can then be effected according to the processes described above for steps (b) through (g) respectively of Scheme A.

Scheme D:

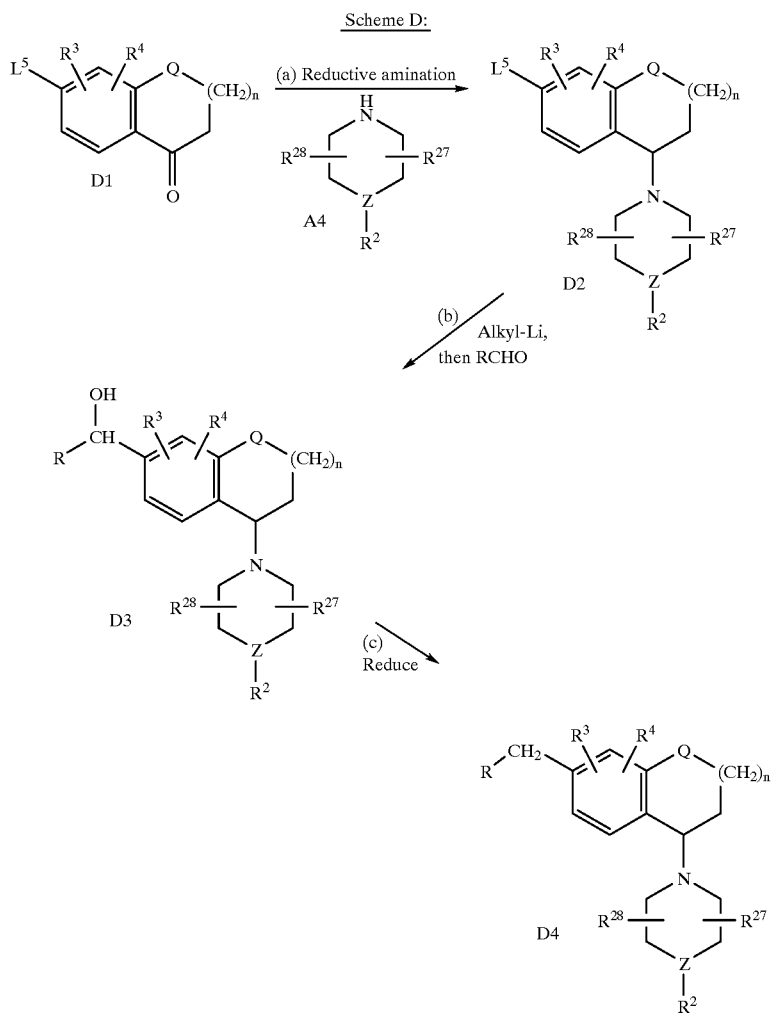

The process of Step (a) (reductive amination) can be carried out according to the alternative condensation/reduction process of Scheme A (described above as an alternative method for preparing compounds of the formulae A5 and A7). The group $L^5$ is preferably a chlorine atom or especially a bromine or iodine atom. The product of the formula $D^2$ can then be reacted with an alkyl-lithium reagent, e.g., n-BuLi or t-BuLi, in an inert anhydrous organic solvent, to replace the group $L^5$ with Li, and the resulting organometallic compound can be reacted with the aldehyde RCHO to yield the compound of the formula D3. The benzylic hydroxy group in D3 can then be reduced, for example with a trialkylsilane, preferably $Et_3SiH$, and a strong acid, preferably trifluoroacetic acid. If the product of the formula D4 is to contain a group $R^1$ or $R^{21}$, this group may be introduced into the compound of the formula D1.

The group $R^2$ in this process is preferably a nitrogen-protecting group, e.g., a benzyloxycarbonyl (CBZ) or especially a t-butyloxycarbonyl (BOC) group. Such a protecting group can be replaced with a group $R^2$ defined above under formula I. A protecting group such as an amidating group can be removed by hydrolysis; e.g., a protecting BOC group can be removed with trifluoroacetic acid or with HCl in EtOAc. The desired group $R^2$ can then be introduced (in one or more steps); for example, a 1-piperidinyl group or N-RY-1-piperidinyl group can be introduced by reductive condensation with a compound of the formula

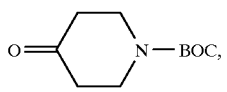

followed by removal of the protecting BOC group by hydrolysis. Both the reductive condensation and the hydrolysis can be effected as described above. Any further substituent $R^y$ (wherein $R^y$ is as defined above) can then be introduced on to the newly liberated nitrogen atom. For example, an amide can be formed by condensation with the acid chloride ($R^y$.Cl, when $R^y$ is an acyl group), if necessary in the presence of a base, or by condensation with the acid itself ($R^y$.OH, when $R^y$ is an acyl group) in the presence of 1-hydroxy-benzotriazole, 1-(3-dimethylaminopropyl)-3-ethylcarbodiimide, and N-methyl-morpholine.

After the process of Scheme A, B, C or D has been carried out, a resulting compound of the formula I wherein Q represents S can be oxidized to a compound wherein Q represents SO or $SO_2$; the oxidizing agent is preferably a peracid such as peracetic acid, 3-chloroperbenzoic acid, or perboric acid, in the presence of a strong acid used in excess, e.g., methanesulfonic acid. If the compound wherein Q is S is being oxidized to the sulfoxide (or the sulfoxide to the sulfone), then about one equivalent of oxidizing agent should be used; if the compound wherein Q is S is being oxidized to the sulfone, then about two equivalents (preferably at least two equivalents) of oxidizing agent should be used.

PHARMACOLOGICAL ACTIVITY

The compounds of formula I exhibit selective m2 and/or m4 muscarinic antagonizing activity, which has been correlated with pharmaceutical activity for treating cognitive disorders such as Alzheimer's disease and senile dementia.

The compounds of formula I display pharmacological activity in test procedures designed to indicate m1, m2 and m4 muscarinic antagonist activity. The compounds are non-toxic at pharmaceutically therapeutic doses. Following are descriptions of the test procedures.

MUSCARINIC BINDING ACTIVITY

The compound of interest is tested for its ability to inhibit binding to the cloned human m1, m2, and m4 muscarinic receptor subtypes. The sources of receptors in these studies were membranes from stably transfected CHO cell lines which were expressing each of the receptor subtypes. Following growth, the cells were pelleted and subsequently homogenized using a Polytron in 50 volumes cold 10 mM Na/K phosphate buffer, pH 7.4 (Buffer B). The homogenates were centrifuged at 40,000×g for 20 minutes at 4° C. The resulting supernatants were discarded and the pellets were resuspended in Buffer B at a final concentration of 20 mg wet tissue/ml. These membranes were stored at −80° C. until utilized in the binding assays described below.

Binding to the cloned human muscarinic receptors was performed using $^3$H-quinuclidinyl benzilate (QNB) (Watson et al., 1986). Briefly, membranes (approximately 8, 20, and 14 μg of protein assay for the m1, m2, and m4-containing membranes, respectively) were incubated with $^3$H- QNB (final concentration of 100–200 pM) and increasing concentrations of unlabeled drug in a final volume of 2 ml at 25° C. for 90 minutes. Non-specific binding was assayed in the presence of 1 μM atropine. The incubations were terminated by vacuum filtration over GF/B glass fiber filters using a Skatron filtration apparatus, and the filters were washed with cold 10 mM Na/K phosphate buffer, pH 7.4. Scintillation cocktail was added to the filters, and the vials were incubated overnight. The bound radioligand was quantified in a liquid scintillation counter (50% efficiency). The resulting data were analyzed for $IC_{50}$ values (i.e. the concentration of compound required to inhibit binding by 50%) using the EBDA computer program (McPherson, 1985). Affinity values ($K_i$) were then determined using the following formula (Cheng and Prusoff, 1973):

$$K_i = \frac{IC_{50}}{1 + \left[\frac{\text{concentration of radioligand}}{\text{affinity}(K_D) \text{ of radioligand}}\right]}$$

Hence a lower value of $K_i$ indicates greater binding affinity.

The above procedure is known in the art and has been the subject of detailed publications.

To determine the degree of selectivity of a compound for binding the m2 receptor, the $K_i$ value for m1 receptors was divided by the $K_i$ value for m2 receptors. A higher ratio indicates a greater selectivity for binding the m2 muscarinic receptor.

MICRODIALYSIS METHODOLOGY

The following procedure is used to show that a compound functions as an m2 antagonist:

Surgery: For these studies, male Sprague-Dawley Rats (250–350 g) were anesthetized with sodium pentobarbital (54 mg/kg, ip) and placed on a Kopf stereotaxic apparatus. The skull was exposed and drilled through to the dura at a point 0.2 mm anterior and 3.0 mm lateral to the bregma. At these coordinates, a guide cannula was positioned at the outer edge of the dura through the drilled opening, lowered perpendicularly to a depth of 2.5 mm, and permanently secured with dental cement to bone screws. Following the surgery, rats were given ampicillin (40 mg/kg, ip) and individually housed in modified cages. A recovery period of approximately 3 to 7 days was allowed before the microdialysis procedure was undertaken.

Microdialysis: All of the equipment and instrumentation used to conduct in vivo microdialysis was obtained from Bioanalytical Systems, Inc. (BAS). The microdialysis procedure required the insertion through the guide cannula of a thin, needle-like perfusable probe (CMA/12.3 mm×0.5 mm) to a depth of 3 mm in striatum beyond the end of the guide. The probe was connected beforehand with tubing to a microinjection pump (CMA-/100). Rats were collared and tethered, and, following probe insertion, were placed in a large clear plexiglass bowl with litter material and access to food and water. The probe was perfused at 2 μl/min with Ringer's buffer (NaCl 147 mM; KCl 3.0 mM; $CaCl_2$ 1.2 mM; $MgCl_2$ 1.0 mM) containing 5.5 mM glucose, 0.2 mM L-ascorbate, and 1 μM neostigmine bromide at pH 7.4. To achieve stable baseline readings, microdialysis was allowed to proceed for 90 minutes prior to the collection of fractions. Fractions (20 μl) were obtained at 10-minute intervals over a 3-hour period using a refrigerated collector (CMA170 or 200). Following the collection of four to five baseline fractions, the drug or combination of drugs to be tested was administered to the animal. Once collection was complete, each rat was autopsied to determine how accurately the probe was placed.

Acetylcholine (ACh) analysis: The concentration of ACh in collected samples of microdialysate was determined using HPLC/electrochemical detection. Samples were auto-injected (Waters 712 Refrigerated Sample Processor) onto a polymeric analytical HPLC column (BAS, MF-6150) and eluted with 50 mM $Na_2HPO_4$, pH 8.5. To prevent bacterial growth, Kathon CG reagent (0.005%) (BAS) was included in the mobile phase. Eluate from the analytical column, containing separated ACh and choline, was then immediately passed through an immobilized enzyme reactor cartridge (BAS, MF-6151) coupled to the column outlet. The reactor contained both acetylcholinesterase and choline oxidase covalently bound to a polymeric backbone. The action of these enzymes on ACh and choline resulted in stoichiometric yields of hydrogen peroxide, which was electrochemically detected using a Waters 460 detector equipped with a platinum electrode at a working potential of 500 mvolts. Data acquisition was carried out using an IBM Model 70 computer equipped with a microchannel IEEE board. Integration and quantification of peaks were accomplished using "Maxima" chromatography software (Waters Corporation).

Total run time per sample was 11 minutes at a flow rate of 1 ml/min. Retention times for acetylcholine and choline were 6.5 and 7.8 minutes respectively. To monitor and correct for possible changes in detector sensitivity during chromatography, ACh standards were included at the beginning, middle and end of each sample queue.

Increases in ACh levels are consistent with presynaptic m2 receptor antagonism.

RESULTS OF THE TESTS

The present invention also relates to achieving similar synergistic results by administering any compound capable of enhancing ACh release, such as a muscarinic antagonist, e.g., scopolamine or QNB, in combination with an acetylcholinesterase inhibitor. Preferably the ACh release-enhancing compound is either an m2 selective muscarinic antagonist, i.e. one having a ratio of ($K_i$ for m1)/($K_i$ for m2) greater than 1, or an m4 selective muscarinic antagonist, i.e. one having a ratio of ($K_i$ for m1)/($K_i$ for m4) greater than 1. The m2 or m4 selective muscarinic antagonists for practicing this aspect of the invention include without limitation 3-α-chloroimperialine, AF-DX 116, AF-DX 384, BIBN 99 (these last three compounds being available from Boehringer-Ingleheim), tripitramine, and himbacine.

The tests reported in the following Table show that the compounds numbered 5, 9, 10, 14 and 15 in particular have useful values of the m1/m2 and m4/m2 ratios and should have valuable properties for the treatment of cognitive disorders.

TABLE 1

ACTIVITIES OF COMPOUNDS OF FORMULA I

| | Compound No. | M.P. °C. | m1 | m1/m2 | m2 | m4 | m4/m2 |
|---|---|---|---|---|---|---|---|
| 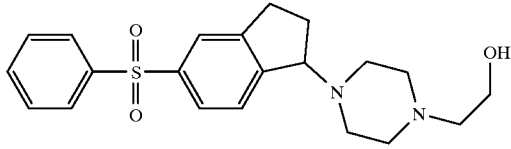 | 1 | | 356 | 4.5 | 79 | 106 | 1.3 |
| 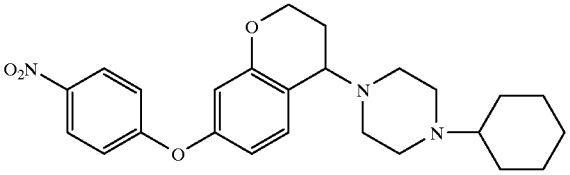 | 2 | 67–68 | 42 | 1.5 | 27 | | |
| 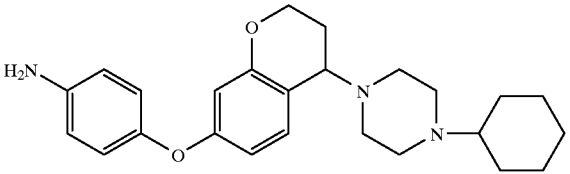 | 3 | 219–221 | 82 | 0.6 | 130 | 37 | 0.3 |
| 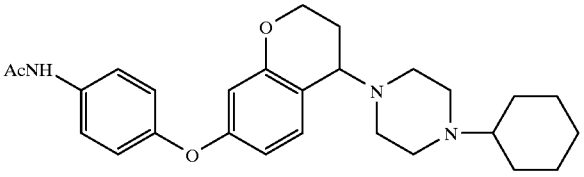 | 4 | 124–126 | 223 | 1.0 | 224 | >200 | >0.9 |
| 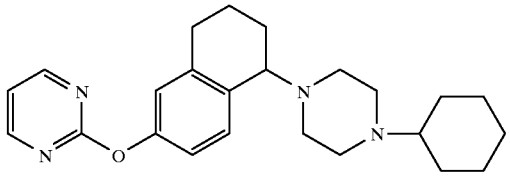 | 5 | 179–181, dimaleate salt | 160 | 7.5 | 21 | 35 | 1.6 |
| 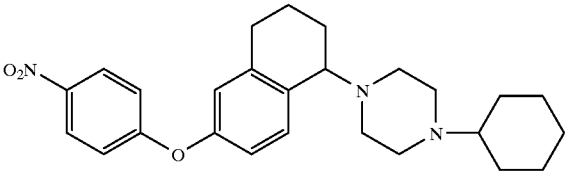 | 6 | 205 (dec.) | 633 | 6.6 | 96 | 77 | 0.8 |

TABLE 1-continued

ACTIVITIES OF COMPOUNDS OF FORMULA I

| Compound No. | M.P. °C. | K$_i$ (nm); m1/m2 & m4/m2 | | | | |
|---|---|---|---|---|---|---|
| | | m1/m2 | | | | m4/m2 |
| | | m1 | m2 | m2 | m4 | m2 |
| 7 | 191–193, HCl salt | 105 | 4.0 | 26 | 21 | 0.8 |
| 8 | 191–193, HCl salt | 88 | 3.3 | 27 | 23 | 0.9 |
| 9 | 204–206, dimaleate salt | 265 | 7.7 | 35 | | |
| 10 | 183–184, HCl salt | 151 | 13.2 | 11.5 | 17 | 1.5 |
| 11 | 181–182, HCl salt | 314 | 3.6 | 88 | | |
| 12 | 150–154, dimaleate salt | 173 | 1.9 | 92 | | |
| 13 | | 67 | 4.0 | 17 | 33 | 2.0 |

TABLE 1-continued

| ACTIVITIES OF COMPOUNDS OF FORMULA I | Compound No. | M.P. °C. | K$_i$ (nm); m1/m2 & m4/m2 | | | | |
|---|---|---|---|---|---|---|---|
| | | | m1 | $\frac{m1}{m2}$ | m2 | m4 | $\frac{m4}{m2}$ |
| (structure) | 14 (Isomer A) | 232, HCl salt | 112 | 18.4 | 6.1 | 16 | 2.6 |
| (structure) | 15 (Isomer B) | 253–254, HCl salt | 1.23 | 11.2 | 0.11 | 0.27 | 2.5 |

TABLE 2

Effect of Compounds of the Invention on Release of Acetyl Choline (ACh) from Striatum of Conscious Rats following Peritoneal Administration

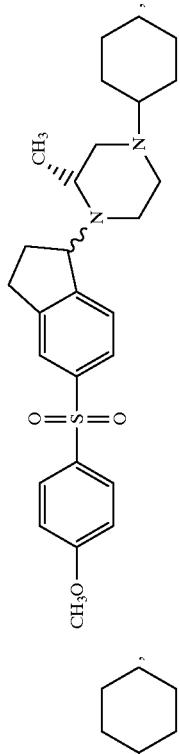

Compound and results

| | Compound 14, Isomer A Dose = 10 mg/kg; 3 rats | | Compound 15, Isomer B Dose = 10 mg/kg; 3 rats | |
|---|---|---|---|---|
| Sample Collection Time (Minutes) | Mean % of baseline | Standard error | Mean % of baseline | Standard error |
| 20 (1) | 99.47 | 0.83 | 98.61 | 1.74 |
| 30 (2) | 100.85 | 4.62 | 93.87 | 0.13 |
| 40 (3) | 99.71 | 3.14 | 102.42 | 1.41 |
| 50 (4) | 99.20 | 1.59 | 103.86 | 3.90 |
| 60 | 100.78 | 4.20 | 102.14 | 4.10 |
| 70 | 86.66 | 6.26 | 175.31 | 6.60 |
| 80 | 95.26 | 4.15 | 278.67 | 31.06 |
| 90 | 95.90 | 1.66 | 266.94 | 17.84 |
| 100 | 102.30 | 16.27 | 245.19 | 16.74 |
| 110 | 108.24 | 13.56 | 217.34 | 9.29 |
| 120 | 85.62 | 16.35 | 222.39 | 20.20 |
| 130 | 103.94 | 13.20 | 205.69 | 12.36 |
| 140 | 99.35 | 13.94 | 188.49 | 11.52 |
| 150 | 91.47 | 11.51 | 189.79 | 13.56 |
| 160 | 90.80 | 20.28 | 184.27 | 13.03 |
| 170 | 89.0 | 12.35 | 189.27 | 23.70 |
| 180 | 83.13 | 10.95 | 189.86 | 12.41 |

Notes:
(1) Control; gives first baseline.
(2) Control; gives second baseline.
(3) Control; gives third baseline.
(4) Compounds were injected at 50 minutes.

Particularly preferred compounds of the formula I include those of the following formulae, and their acid addition salts:

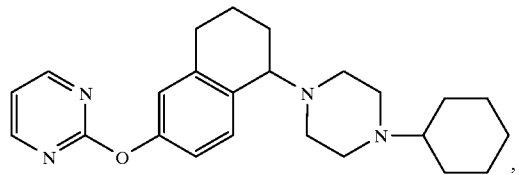
,

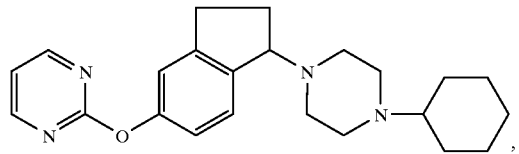
,
and

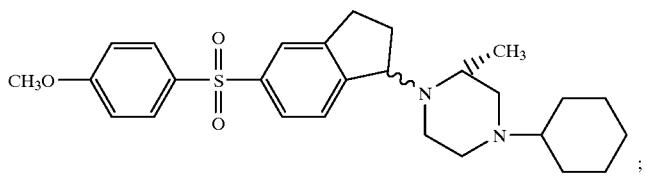
;

and also the compounds of the following formulae, and their acid addition salts:

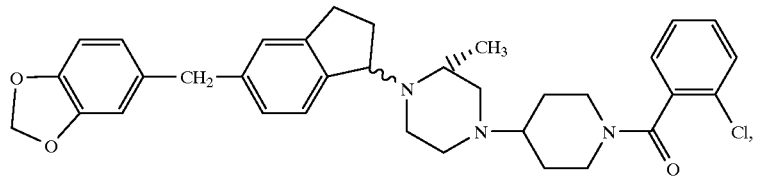
,

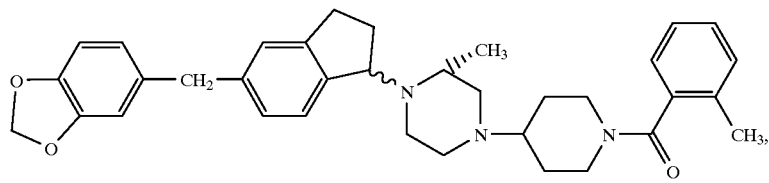
,

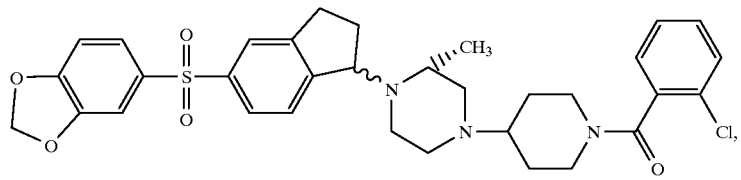
, and
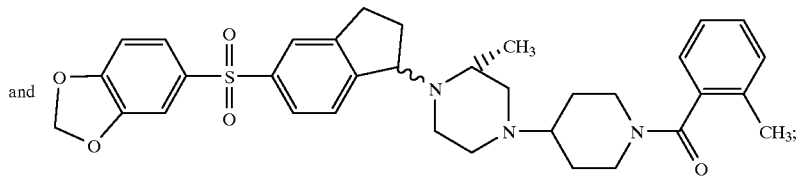
;

in all of these compounds, the methyl group attached to the piperazine ring (where present) is in the (R)-conformation.

Pharmaceutical compositions can be prepared from the compounds of formula I, which are capable of enhancing ACh release, by admixing them with pharmaceutically acceptable, inert carriers. Acetylcholinesterase inhibitors can be used as optional constituents of such pharmaceutical compositions to provide a better, frequently even synergistic, effect. The pharmaceutically acceptable carriers may be either solid or liquid. Preparations in solid form include powders, tablets, dispersible granules, capsules, cachets and suppositories. A solid carrier can be one or more substances which may also act as diluents, flavoring agents, solubilizers, lubricants, suspending agents, binders or tablet-disintegrating agents; it may also be an encapsulating material.

Preparations in liquid form include solutions, suspensions and emulsions. As an example may be mentioned solutions in water or in water-propylene glycol for parenteral injection.

Also included are preparations in solid form which are intended for conversion, shortly before use, to liquid form preparations for either oral or parenteral administration. Such liquid forms include solutions, suspensions and emulsions. The solid forms are most conveniently provided in unit dose form for this purpose and are used to provide a single liquid dosage unit.

The invention also contemplates alternative delivery systems including, but not necessarily limited to, transdermal delivery. The transdermal compositions can take the form of creams, lotions and/or emulsions and can be included in transdermal patches of the matrix or reservoir type as are conventional in the art for this purpose.

Preferably, the pharmaceutical preparation is in unit dosage form. In such form, the preparation is subdivided into unit doses containing appropriate quantities of the active components. The unit dosage form can be a packaged preparation, the package containing discrete quantities of preparation such as packeted tablets, capsules and powders in vials or ampoules. The unit dosage form can also be a capsule, cachet or tablet itself, or it may be the appropriate number of any of these in a packaged form.

The quantity of active compound in a unit dose preparation may be varied or adjusted from 1 mg to 100 mg according to the particular application and the potency of the active ingredient and the intended treatment. This would correspond to a dose of about 0.001 to about 20 mg/kg, which may be divided over 1 to 3 administrations per day. The composition may, if desired, also contain other therapeutic agents.

The dosages may be varied, depending on the requirement of the patient, the severity of the treated condition, and the particular compound administered. Determination of the proper dosage for a particular situation is within the skill of those in the medical art. For convenience, the total daily dosage may be divided and administered in portions throughout the day or by means providing continuous delivery.

When a compound of formula I or a compound capable of enhancing ACh release is used in combination with an acetylcholinesterase inhibitor to treat cognitive disorders, these two active components may be co-administered simultaneously or sequentially. Alternatively, a single pharmaceutical composition comprising a compound of formula I or a compound capable of enhancing ACh release and an acetylcholinesterase inhibitor in a pharmaceutically acceptable carrier can be administered. The components of the combination can be administered individually or together in any conventional oral or parenteral dosage form, such as capsule, tablet, powder, cachet, suspension, solution, suppository, nasal spray, etc. The dosage of the acetylcholinesterase inhibitor may range from 0.001 to 100 mg/kg body weight.

The invention disclosed herein is exemplified by the following Examples, which should not be construed to limit the scope of the disclosure. Alternative mechanistic pathways and analogous structures may be apparent to those skilled in the art.

EXAMPLES

Example 1

Step A

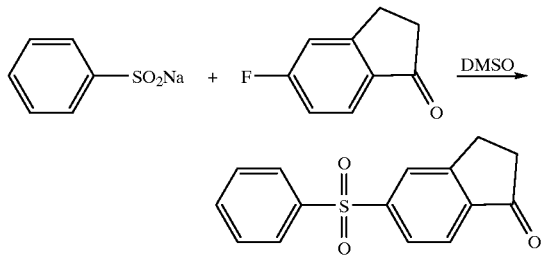

4.2 g (29 mmoles) of 5-fluoroindanone and 5.05 g (31 mmoles) of sodium benzenesulfinate were combined in dry DMSO (20 mL). The mixture was heated to about 120° C. for 48 hours, cooled to room temperature, and poured into ice water (300 mL). The precipitate that developed was filtered off and triturated with 100 mL dry ether, then filtered off again and dried in vacuo to give 1.57 g (20% yield) of the desired sulfone as a brown powder. This was used directly in the next reaction.

Step B

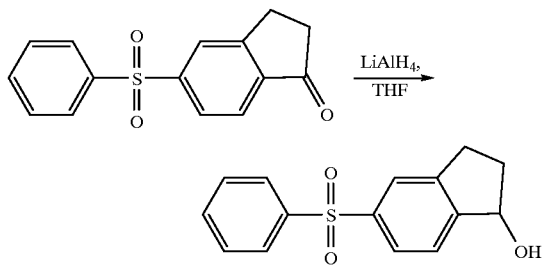

1.07 g (3.9 mmoles) of 5-phenylsulfonylindanone was taken up in dry THF (20 mL) at room temperature. A 1M solution of lithium aluminum hydride in THF (3.9 mL) was added slowly. The resulting mixture was stirred for one hour at room temperature, and quenched cautiously with 2M sodium hydroxide solution and then with water. Solid potassium carbonate was added, and the mixture was stirred until the salts formed a granular precipitate. This was filtered off and washed with ether, and the organic solvents were evaporated to give 0.998 g of the desired alcohol (92%), which was sufficiently pure for the next reaction.

Step C

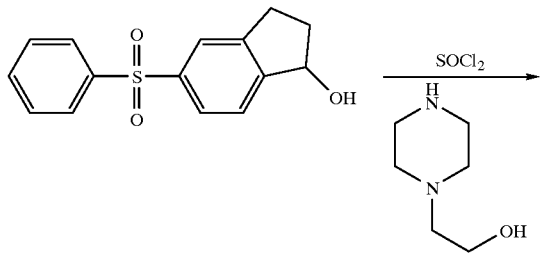

-continued

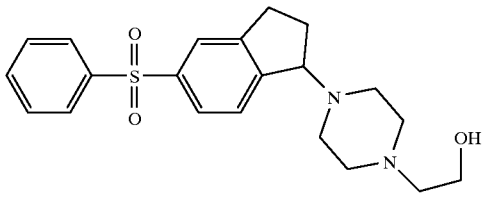

0.700 g (2.55 mL) of the starting indanyl alcohol were taken up in neat thionyl chloride (2 mL), and the resulting mixture was stirred at room temperature for one hour. The volatiles were removed on a rotary evaporator, and the crude chloride was taken up in DMF (5 mL) with N-hydroxyethyl piperazine (0.94 mL, 3 equiv.). This mixture was heated to about 60° C. for 16 hours, cooled to room temperature, and poured into ice water (100 mL). The crude product was extracted with methylene chloride, the organic layers were dried and evaporated, and the residue was purified by column chromatography on silica gel. The column was eluted with ethyl acetate containing 5% methanol and then with ethyl acetate containing 5% methanol and 2% triethylamine to give the desired product.

Example 2

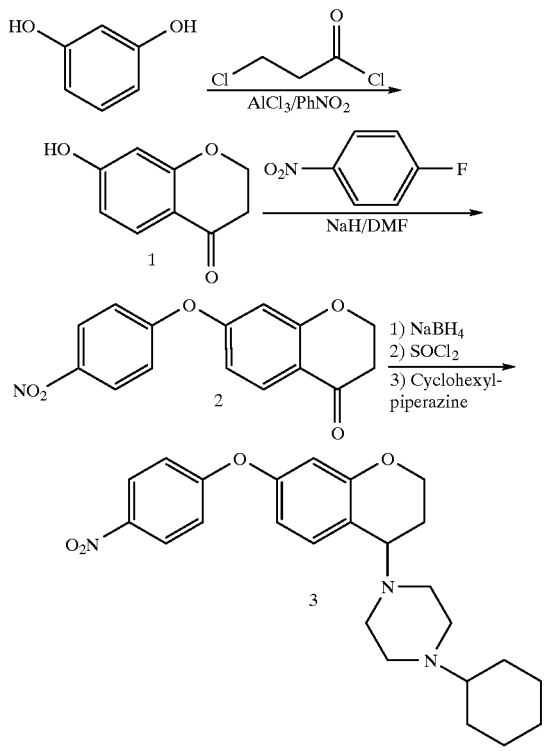

6-Hydroxy-4-chromanone, 1:

A solution of resorcinol (11.0 g) in nitrobenzene (120 mL) at 5° C. was treated dropwise with βchloropropionyl chloride (12.7 g) with stirring. Anhydrous $AlCl_3$ (31 g) was added portionwise with stirring, and the temperature was kept below 15° C. After 15 minutes the mixture was heated to 40–45° C. and kept there with stirring for 3 hours longer; it was then cooled to room temperature and allowed to stand overnight. The reaction mixture was poured with stirring into crushed ice (200 g) containing conc. HCl (10 mL). This was extracted with ether and the organic layer was extracted with 5% NaOH. The basic layer was made acidic with conc. HCl. A tar-like solid separated out and was recrystallized from hot water to yield a white solid, m.p. 138–142° C.

7-(4'-Nitrophenoxy)-4-chromanone, 2:

A solution of 6-hydroxychromanone (1.64 g, 10 mmol) in DMF (10 mL) was treated with NaH (10 mmole, 60% in mineral oil) with stirring. After 30 minutes it was treated with a solution of 4-fluoronitrobenzene in DMF (5 ml) and stirred at 90° C. for 6 hours. After cooling, it was diluted with ice water (75 mL) and then extracted with EtOAc (2×50 mL). Evaporation of the dried organic layer gave a gum-like residue (1.9 g). This crude product was used in the next step without further purification.

1-Cyclohexyl-4-[7-[(4-nitrophenyl)oxy]-chroman-4-yl]-piperazine, 3:

Crude 7-(4'-nitrophenyloxy)-4-chromanone (1.9 g) in EtOH (150 mL) was reduced with $NaBH_4$ (250 mg) at room temperature overnight. The crude product was purified through a column of silica gel (EtOAc:$CH_2Cl_2$, 2:8) to give pure 7-(4'-nitrophenyloxy)-4-chromanol (550 mg). This compound (550 mg) was converted to the chloride with thionyl chloride (0.28 g) in $CH_2Cl_2$ (30 mL) at 0° C. for 1 hour and then at room temperature for 3 hours. Work-up yielded crude 4-chloro-7-(4'-nitrophenyloxy)-chroman (500 mg). This was heated with N-cyclohexylpiperazine (0.9 g) at 130° C. for one hour. The mixture was then diluted with water (35 mL), made basic with $K_2CO_3$ and extracted with EtOAc. The residue from evaporation of the dried organic layer was purified through a column of TLC-grade silica gel (35 g). The desired product was recrystallized rom acetonitrile, m.p. 67–68° C.

Example 3

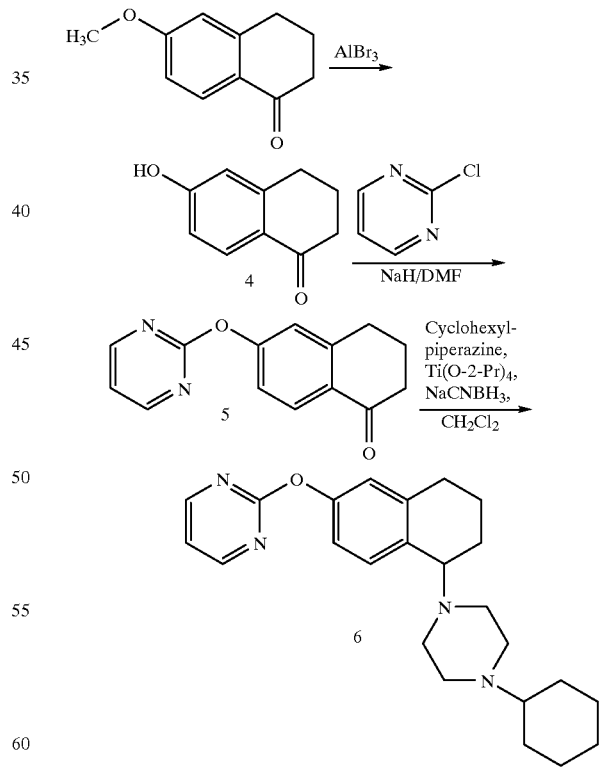

6-Hydroxytetralone, 4:

A solution of 6-methoxytetralone (35 mmol), and $AlBr_3$ (75 mmol) in toluene (250 mL) was heated on an oil bath at 100° C. for 5 to 6 hours. The solution was cooled to room temperature and then poured onto a mixture of 1N HCl (200 mL) and crushed ice (500 g). This was stirred with EtOAc (300 mL) and filtered through a sintered glass funnel. The filtrate was transferred to a separatory funnel and the aqueous layer was extracted with EtOAc (2×100 mL). The organic layers were combined and dried with $MgSO_4$, filtered and evaporated to a solid, 6-hydroxytetralone, which was pure by NMR and TLC (1:1 hexane:EtOAc).

6-[(2-Pyrimidinyl)oxyl-tetralone, 5:

6-Hydroxytetralone (31 mmol) was dissolved in dry DMF (50 mL), chilled in an ice/water bath and blanketed with a stream of nitrogen. NaH (60% in mineral oil, 31 mmol) was added slowly and in portions. Once gas evolution ceased, 2-chloropyrimidine (31 mmol) was added, the ice bath was removed and the solution heated at 100° C. for 1.5 hours. It was then cooled to room temperature and the solvent was removed in vacuo. The residue was treated with water and $CH_2Cl_2$ (200 mL each). Evaporation of the organic layer yielded crude material which was purified by flash chromatography (1:1 hexane:EtOAc) to afford 6-[(2-pyrimidinyl) oxyl-tetralone as a light yellow powder.

4-Cyclohexyl-1-piperazinyl-[6-[(2-pyrimidinyl)oxy]]-1,2,3,4-tetrahydro-naphthalene, 6:

6-[(2-Pyrimidinyl)oxy]-tetralone (3.2 mmol), N-cyclohexylpiperazine (3.2 mmol) and $Ti(O-2-Pr)_4$ (3.2 mmol) were dissolved in $CH_2Cl_2$ (10 mL). The solution was stirred at room temperature for 20 hours and then quenched with $NaCNBH_3$ (6.4 mmol in 5 mL EtOH). Water (20 mL) was added, the resulting mixture was filtered through a pad of 'Celite', and the residue was rinsed with $CH_2Cl_2$ (10 mL). The organic layer was dried with $Na_2SO_4$ and evaporated to yield the crude product as an oil. Purification by column chromatography on TLC-grade silica gel and 100:3:1 $CH_2Cl_2$:EtOH:$NH_4OH$ as eluant gave the pure product, 4-cyclohexyl-1-piperazinyl-[6-[(2-pyrimidinyl)oxy]]-1,2,3,4-tetrahydro-naphthalene. This was converted to the dimaleate salt, m.p. 179–181.5° C., by dissolving in EtOAc and heating with 2 equivalents of maleic acid.

Example 4

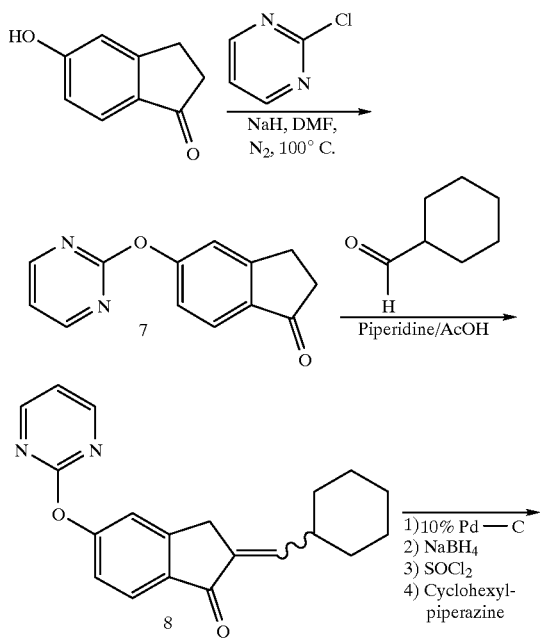

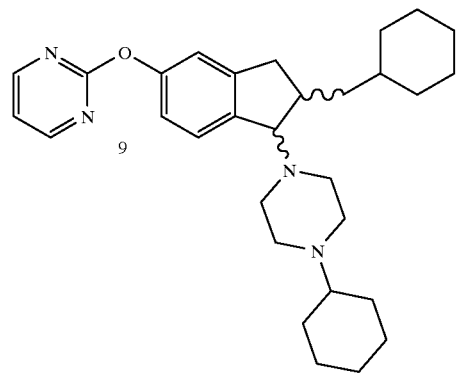

5-((2-Pyrimidinyl)oxy)indanone:

5-Hydroxyindanone (3.2 g, 21.6 mmol) was dissolved in dry DMF (20 mL) in a 3-neck flask fitted with an $N_2$ inlet and reflux condenser. The system was blanketed with $N_2$, and 60% NaH in mineral oil (860 mg) was added slowly and in portions at 0° C. Then 2-chloropyrimidine (2.5 g) was added, the ice bath was replaced with an oil bath, and the solution was heated at 100° C. for 3 hours. This was then cooled to room temperature before removal of DMF in vacuo. To the residue was added water (50 mL), the mixture was extracted with $CH_2Cl_2$ (50 mL), and the aqueous layer extracted twice more with $CH_2Cl_2$. The organic layer was extracted with 1N NaOH (50 mL) to remove unreacted phenol and then dried with $Na_2SO_4$ and evaporated to a dark brown solid (3.6 g). The solid was extracted with EtOAc; filtration removed an insoluble precipitate. The filtrate was dried as before and evaporated to yield the product which was pure by NMR and TLC (1:1 hexane:EtOAc).

2-(2-(Cyclohexylmethyl)-3H-1-oxo-inden-5-yl) pyrimidine. 8:

To piperidine (0.25 mL) at 0° C. was added acetic acid (0.2 mL) followed by cyclohexanecarboxaldehyde (918 mg, 8.2 mmol) and 5-[(2-pyrimidinyl)oxy]-indanone, 7 (1.85 g, 8.2 mmol) (synthesized by the same route as 5 above). The mixture was heated at 100° C. for 25 minutes. Methanol (20 mL) was added to the hot solution, which, after cooling, was concentrated in vacuo. The residue was treated with water and $CH_2Cl_2$ (20 mL each), and the organic layer was dried with $Na_2SO_4$. Evaporation of the solvent gave the crude material as a dark brown oil. Purification by flash chromatography with 1:1 hexane:ethyl acetate resulted in the pure enone, 8.

2-(2-(Cyclohexylmethyl)-2,3-dihydro-1-oxo-indan-5-yl) pyrimidine:

The enone was cleanly reduced to the saturated ketone with 10% Pd-C catalyst (100 mg) on a Parr apparatus for 45 minutes. The catalyst was filtered off to yield the saturated ketone.

Alternative Reduction of Ketone (general procedure)

The ketone (1 equivalent) is dissolved in EtOH and $NaBH_4$ (0.75 equivalent) is added. This is stirred at room temperature and monitored by TLC (1:1 Hexane:EtOAc) until all ketone has disappeared (about 2 to 4 hours) and the reaction is complete. Then the EtOH is removed in vacuo and the residue treated with an equal amount of $CH_2Cl_2$ and water. The organic layer is dried with $Na_2SO_4$ and the solvent is evaporated off to yield the crude alcohol, which is used directly without purification.

Conversion of Alcohol to Chloride (general procedure)

The alcohol (1 equivalent) is dissolved in $CH_2Cl_2$ and chilled in an ice water bath. Thionyl chloride (1.2 equivalents) is then added and the solution stirred under a $CaSO_4$ drying tube and monitored by TLC (25% EtOAc in Hexane) until the alcohol has disappeared. An equivalent amount of water is added and the mixture is basified to pH 8 with solid $NaHCO_3$. The aqueous layer is extracted with $CH_2Cl_2$. The organic extracts are combined, dried and evaporated to provide the crude chloride, which is used without further purification.
2-[[1-(4-Cyclohexyl-1-piperazinyl)-2-(cyclohexylmethyl)-2,3-dihydro-1H-inden-5-yl]oxy]pyrimidine, 9:

The chloride (1 equivalent) and cyclohexylpiperazine were dissolved in $CH_3CN$, refluxed for 2 hours, and then cooled to room temperature. Water was added and the mixture was extracted with EtOAc (4x). The organic extracts were dried and evaporated to yield the crude product which was purified by column chromatography using TLC-grade silica gel and EtOAc as eluant.

2-[[1-(4-Cyclohexyl-1-piperazinyl)-2-(cyclohexylmethyl)-2,3-dihydro-1H-iden-5-yl]oxy]pyrimidine dimaleate was a mixture of diastereomers (proportions unknown), m.p. 150–154° C.

Example 5

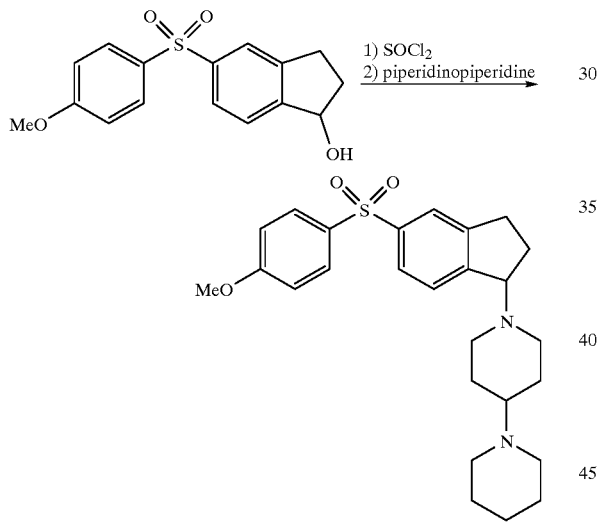

The alcohol (0.4 g) was treated with thionyl chloride (20 mL) at ambient temperature for 3 hours. Thionyl chloride was removed under vacuum, the crude product was treated with piperidinopiperidine (1.22 g), and the reaction mixture heated overnight at 130° C. At the end of this time the reaction mixture was cooled to ambient temperature, diluted with dichloromethane and washed with 10% sodium hydroxide solution. The crude product was purified on silica gel (triethylamine:ethyl acetate 1:20) to give the desired product (0.05 g). HRMS for $C_{26}H_{35}N_2O_3S$: Calcd.: 455.2368; Found: 455.2373.

Example 6

2-[[1-(4-Cyclohexyl-1-piperazinyl)-2-(cyclohexylmethyl)-2,3-dihydro-1 H-inden-5-yl]oxy]pyrimidine, 9:x

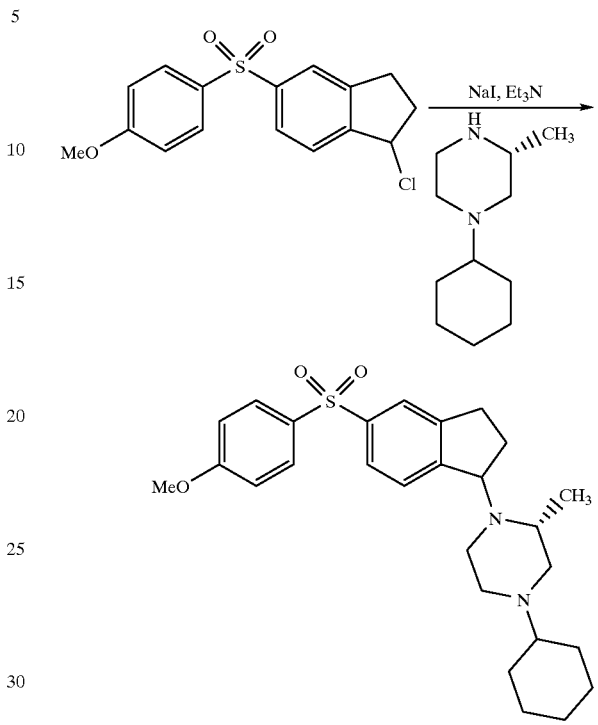

The chloride (0.6 g, 2.0 mmol) (from the first crude product of the process of Example 5), DMF (10 mL), sodium iodide (1.8 g), triethylamine (0.21 g) and piperazine (0.38 g, 2.0 mmol) were heated overnight at 50° C., and stirred for an additional 2 hours at 70° C. The reaction mixture was then cooled to room temperature and diluted with ethyl acetate. The solution was washed with 10% $Na_2CO_3$, water and brine, and then concentrated to yield a mixture of two diastereomers. Separation was carried out by chromatography on silica gel using ethyl acetate; diastereomer $R_f$ for Isomer A (compound 14, Table 1)=0.3, and for Isomer B (compound 15, Table 1)=0.4.

Further compounds that are described in the Tables or listed by formula immediately after the Tables can be prepared by analogous methods.

While a number of embodiments of this invention are described herein, it is apparent that the embodiments can be altered to provide other embodiments that utilize the compositions and processes of this invention. Therefore, it will be appreciated that the scope of this invention includes alternative embodiments and variations which are defined in the foregoing Specification; and the invention is not to be limited to the specific embodiments that have been presented herein by way of example.

We claim:

1. A compound having the structural formula or a stereoisomer thereof, or a pharmaceutically acceptable salt, or solvate thereof,
wherein:

Z is N;

X is —O—, —S—, —SO—, —SO$_2$—, —CO—, —CH$_2$—, —CONR$^{20}$—, —NR$^{20}$—SO$_2$—, —NR$^{20}$CO—, or —SO$_2$—NR$^{20}$—;

Q is —O—, —S—, —SO—, —SO$_2$—, or —CH$_2$—;

R is $R^1$ and $R^{21}$ are independently selected from the group consisting of hydrogen, alkyl, alkenyl, cycloalkyl, cycloalkenyl, cycloalkylalkyl, cycloalkenylalkyl, phenylalkyl, and hydroxyalkyl;

$R^2$ is cycloalkyl, cycloalkyl substituted with 1 to 3 independently selected $R^3$ groups, cycloalkenyl, cycloalkylalkyl, (wherein $R^y$ is H, alkyl, alkenyl, SO$_2$R$^z$ or COR$^z$ wherein $R^z$ is alkyl, aryl or cycloalkyl);

$R^3$, $R^4$, $R^5$, $R^6$, $R^{22}$, $R^{24}$, and $R^{25}$ are independently selected from the group consisting of H, alkyl, halo, alkoxy, benzyloxy, benzyloxy substituted by nitro or aminoalkyl, polyhaloalkyl, nitro, hydroxy, amino, alkylamino, formyl, alkylthio, acyloxy, alkylsulfonyl, arylsulfonyl, acyl, alkoxycarbonyl, alkylsulfinyl, —OCONH$_2$, —OCONH— alkyl, —OCON(alkyl)$_2$, —NHCOO— alkyl, —NHCO— alkyl, phenyl, hydroxyalkyl, and 1-morpholinyl;

$R^8$ is hydrogen, lower alkyl or cyclopropyl;

$R^{20}$ is H, phenyl or alkyl; and $R^{27}$ and $R^{28}$ are independently selected from the group consisting of H, alkyl, hydroxyalkyl, alkoxyalkyl, arylalkyl, mercaptoalkyl, alkylthioalkyl, and carboxyalkyl, and additionally $R^{27}$ and $R^{28}$ may be joined to form an alkylene group; and n is 0 or an integer from 1 to 3.

2. A compound of claim 1, wherein Z is N, Q is —CH$_2$— and n is 0, 1 or 2.

3. A compound of claim 1, wherein X is O, SO or SO$_2$.

4. A compound of claim 1, wherein R is wherein $R^5$ and $R^6$ are H, CH$_3$, nitro, NH$_2$, acetylamino, or methoxy.

5. A compound of claim 4, wherein $R^1$ is H, cycloalkyl, cycloalkylalkyl or alkyl and $R^{21}$ is H.

6. A compound of claim 5, wherein $R^1$ is H.

7. A compound of claim 4, wherein X is O or SO$_2$, $R^3$ and $R^4$ are H, $R^1$ is H, cycloalkyl, cycloalkylalkyl or alkyl, $R^{21}$ is H, and R is 2-pyrimidinyl or 4-methoxyphenyl.

8. A compound of claim 7, wherein Z is N, $R^1$ is H or cyclohexylmethyl, and $R^2$ is cyclohexyl.

9. A compound of claim 8, wherein at least one of $R^{27}$ and $R^{28}$ is alkyl and he other is H or alkyl.

10. A compound of claim 9, wherein one of $R^{27}$ and $R^{28}$ is methyl or hydrogen and the other is hydrogen.

11. A compound of claim 1, wherein:

R is a phenyl group, which may be substituted with nitro, NH$_2$, acetylamino, or methoxy, or R is a 2-pyrimidinyl group;

X is S, SO, SO$_2$ or O;

Q is CH$_2$ or O;

n is 0, 1 or 2;

$R^{21}$ is H and $R^1$ is H or cyclohexylmethyl;

$R^{27}$ and $R^{28}$ are H or CH$_3$;

Z is N; and $R^2$ is cyclohexyl.

12. A compound of claim 11, wherein:

R is a 4-methoxyphenyl group or a 2-pyrimidinyl group;

X is SO$_2$ or O;

Q is CH$_2$; and n is 0.

13. A compound selected from the group consisting of the following formulae:

-continued

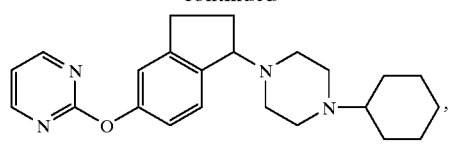
5 and

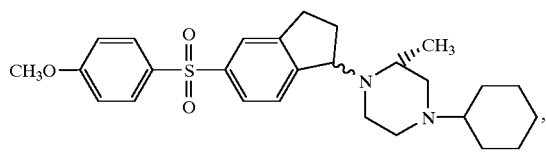
10

15 wherein the methyl group attached to the piperazine ring is in the (R)-conformation.

14. A compound selected from the group consisting of the following formulae:

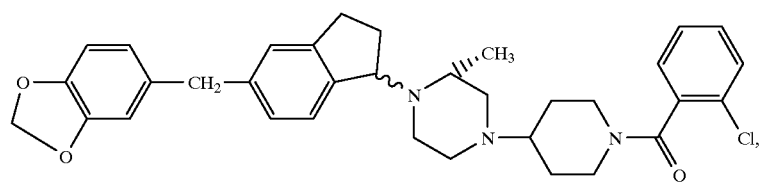

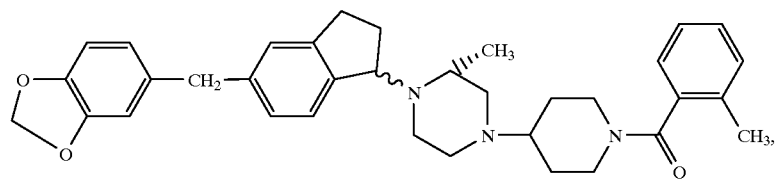

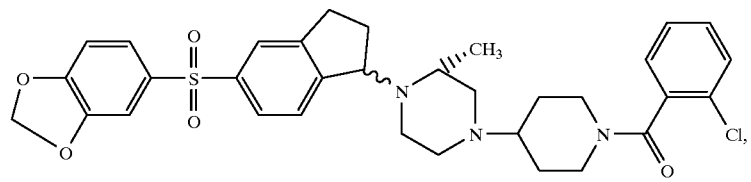

and 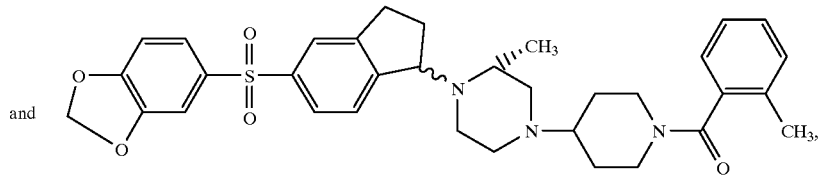

wherein the methyl group attached to the piperazine ring is in the (R)-conformation.

15. A pharmaceutical composition which comprises a compound as defined in claim 1 in combination with a pharmaceutically acceptable carrier.

16. A method for improving memory and learning in patients suffering from Alzheimer's disease comprising administering to a patient suffering from said disease an effective amount of a compound of claim 1.

* * * * *